(12) United States Patent
Aslanian et al.

(10) Patent No.: US 7,482,468 B2
(45) Date of Patent: Jan. 27, 2009

(54) IMIDAZOLE AND BENZIMIDAZOLE DERIVATIVES USEFUL AS HISTAMINE $H_3$ ANTAGONISTS

(75) Inventors: Robert G. Aslanian, Rockaway, NJ (US); Wing C. Tom, Cedar Grove, NJ (US); Xiaohong Zhu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/334,932

(22) Filed: Jan. 19, 2006

(65) Prior Publication Data

US 2006/0166960 A1  Jul. 27, 2006

Related U.S. Application Data

(60) Provisional application No. 60/646,094, filed on Jan. 21, 2005.

(51) Int. Cl.
*C07D 403/10* (2006.01)
*C07D 403/14* (2006.01)
*C07D 221/04* (2006.01)

(52) U.S. Cl. .................. 548/306.1; 546/194
(58) Field of Classification Search .............. 548/306.1; 546/194
See application file for complete search history.

(56) References Cited

U.S. PATENT DOCUMENTS

2005/0197328 A1\* 9/2005 Bailey et al. ................ 514/218

FOREIGN PATENT DOCUMENTS

| WO | WO0240467 | \* | 5/2002 |
| WO | WO 03/080610 A1 | | 10/2003 |
| WO | WO 03/088967 A1 | | 10/2003 |

OTHER PUBLICATIONS

Vippagunta, et al. Crystalline solids. Advanced Drug Delivery Reviews. (2001), 48, pp. 3-26.\*
Faghih, Ramin, et al., "Aminoalkoxybiphenylnitriles as Histamine-3 Receptor Ligands", Bioorganic & Medicinal Chemistry Letters 12:3077-3079 (2002).
PCT International Search Report dated Jun. 21, 2006 for corresponding PCT Application No. PCT/US2006/001832.

\* cited by examiner

*Primary Examiner*—Kamal A Saeed
*Assistant Examiner*—Shawquia Young
(74) *Attorney, Agent, or Firm*—Mark W. Russell; Jeffrey P. Bergman

(57) ABSTRACT

Disclosed are compounds of the formula

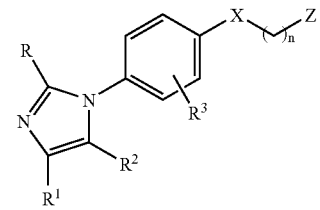

or a pharmaceutically acceptable salt or solvate thereof, wherein:
n is 2-5;
R is $R^3$-aryl, $R^3$-heteroaryl, $R^3$-cycloalkyl, $R^3$-heterocycloalkyl, alkyl, haloalkyl, —$OR^4$, —$SR^4$ or —$S(O)_{1-2}R^5$;
$R^1$ and $R^2$ are H or optionally substituted phenyl or optionally substituted

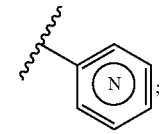

and X is —O— or —S—;
or $R^1$ and $R^2$, together with the carbon atoms to which they are attached form optionally substituted

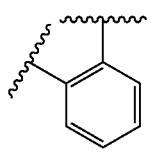 or 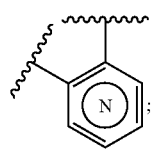

and X is —O—, —S— or —$NR^7$—;
Z is

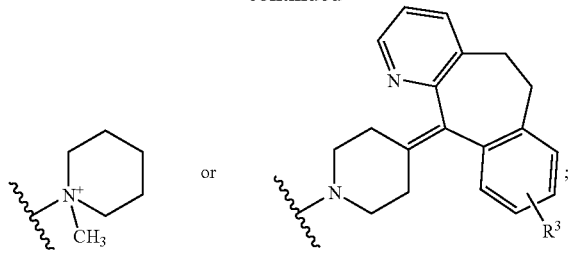

and the remaining variables are as defined in the specification;

also disclosed are pharmaceutical compositions comprising the compounds of formula I;

also disclosed are methods of treating allergy, allergy-induced airway responses, congestion, obesity and metabolic syndrome using the compounds of Formula I, as well as combinations with other drugs useful for treating those diseases.

14 Claims, No Drawings

IMIDAZOLE AND BENZIMIDAZOLE DERIVATIVES USEFUL AS HISTAMINE H₃ ANTAGONISTS

CROSS REFERENCE TO RELATED APPLICATIONS

This application claims the benefit of U.S. Provisional application 60/646,094, filed Jan. 21, 2005.

FIELD OF THE INVENTION

The present invention relates to novel substituted imidazole and benzimidazole derivatives useful as histamine $H_3$ antagonists. The invention also relates to pharmaceutical compositions comprising said compounds and their use in treating inflammatory diseases, allergic conditions, obesity, metabolic syndrome and central nervous system disorders. The invention also relates to the use of a combination of novel histamine $H_3$ antagonists of this invention with histamine $H_1$ compounds for the treatment of inflammatory diseases and allergic conditions, as well as pharmaceutical compositions comprising a combination of one or more novel histamine $H_3$ antagonist compounds of the invention with one or more histamine $H_1$ compounds.

BACKGROUND OF THE INVENTION

The histamine receptors, $H_1$, $H_2$, $H_3$ and $H_4$ are well-identified forms. The $H_1$ receptors are those that mediate the response antagonized by conventional antihistamines. $H_1$ receptors are present, for example, in the ileum, the skin, and the bronchial smooth muscle of humans and other mammals. Through $H_2$ receptor-mediated responses, histamine stimulates gastric acid secretion in mammals and the chronotropic effect in isolated mammalian atria. $H_4$ receptors are expressed primarily on eosinophils and mast cells and have been shown to be involved in the chemotaxis of both cell types.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilation.

Imidazole $H_3$ receptor antagonists are well known in the art. More recently, non-imidazole $H_3$ receptor antagonists have been disclosed in U.S. Pat. No. 6,720,328, and in US Published Applications 2003/0109564, 2004/0097483, 2004/0048843 and 2004/0019099.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

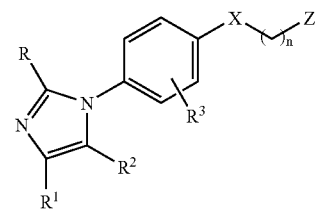

or a pharmaceutically acceptable salt or solvate thereof, wherein:

n is 2, 3, 4 or 5

R is $R^3$-aryl, $R^3$-heteroaryl, $R^3$-cycloalkyl, $R^3$-heterocycloalkyl, alkyl, haloalkyl, —$OR^4$, —$SR^4$ or —$S(O)_{1-2}R^5$;

$R^1$ is H and $R^2$ is $R^6$-phenyl or

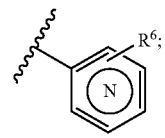

or $R^1$ is $R^6$-phenyl or

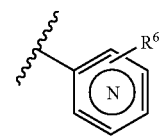

and $R^2$ is H; or $R^1$ and $R^2$ are independently selected from the group consisting of $R^6$-phenyl and

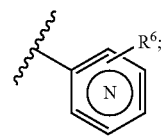

and X is —O— or —S—;

or $R^1$ and $R^2$, together with the carbon atoms to which they are attached form

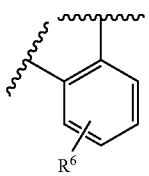 or 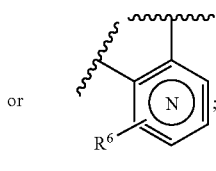

and X is —O—, —S— or —$NR^7$—;

Z is

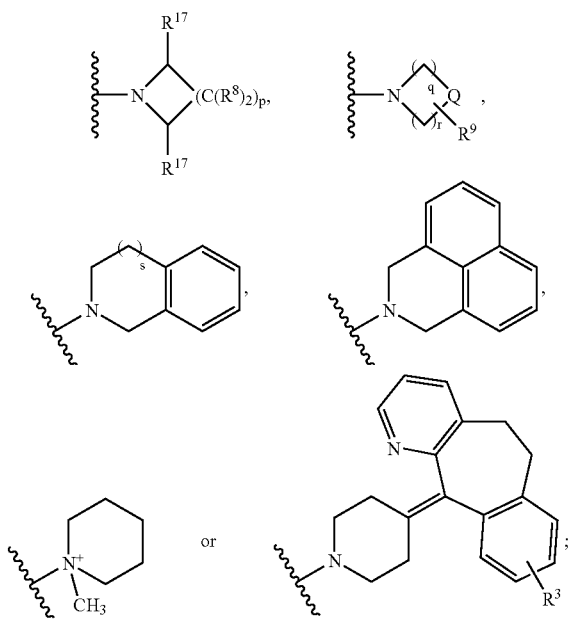

p is 1-5;
Q is —N(R$^{10}$)—, —S— or —O—;
q is 1-4 and r is 1-4, provided that the sum of q and r is 3-6;
s is 1 or 2;
R$^3$ is 1-3 substituents independently selected from the group consisting of H, alkyl, halo, OH, alkoxy and —NR$^{11}$R$^{12}$;
R$^4$ is alkyl, arylalkyl or cycloalkyl;
R$^5$ is alkyl, —NR$^{11}$R$^{12}$, R$^3$-aryl or R$^3$-arylalkyl;
R$^6$ is 1-3 substituents independently selected from the group consisting of H, alkyl, —CF$_3$, halo, —NO$_2$, —CN, —C(O)OR$^{13}$, —C(O)NR$^{11}$R$^{12}$, —NR$^{14}$R$^{15}$, —OR$^{13}$ and haloalkyl;
R$^7$ is H, alkyl, —C(O)OR$^{13}$, —C(O)NR$^{11}$R$^{12}$ or —C(O)R$^{13}$;
each R$^8$ is independently selected from the group consisting of H, alkyl, cycloalkyl, R$^3$-aryl, R$^3$-arylalkyl, R$^3$-heteroaryl, R$^3$-heteroarylalkyl, heterocycloalkyl, heterocycloalkylalkyl, —OR$^{13}$, —C(O)OR$^{13}$, —NR$^{14}$R$^{15}$, —C(O)NR$^{11}$R$^{12}$, —C(O)R$^{16}$, —C(=NOR$^{13}$)aryl and —C(=NOR$^{13}$)heteroaryl; or two R$^8$ groups on the same carbon form a methylenedioxy or ethylenedioxy ring;
R$^9$ is 1-3 substituents independently selected from the group consisting of H, alkyl and cycloalkyl;
R$^{10}$ is H, alkyl, cycloalkyl, R$^3$-aryl, R$^3$-arylalkyl, R$^3$-heteroaryl, R$^3$-heteroarylalkyl, heterocycloalkyl, heterocycloalkylalkyl, —(CH$_2$)$_t$—C(O)OR$^{13}$, —C(O)NR$^{11}$R$^{12}$, —C(O)R$^{16}$, —C(S)R$^{16}$ or —C(=NOR$^{11}$)R$^{16}$;
t is 0, 1 or 2;
R$^{11}$ and R$^{12}$ are independently selected from the group consisting of H, alkyl, cycloalkyl, aryl and arylalkyl;
R$^{13}$ is H, alkyl, cycloalkyl or arylalkyl;
R$^{14}$ is H, alkyl, cycloalkyl or arylalkyl;
R$^{15}$ is H, alkyl, cycloalkyl, —C(O)OR$^{13}$, —C(O)NR$^{11}$R$^{12}$ or —C(O)R$^{13}$;
R$^{16}$ is H, alkyl, R$^3$-cycloalkyl, R$^3$-aryl, R$^3$-arylalkyl or R$^3$-heteroaryl; and
each R$^{17}$ is independently selected from the group consisting of H, alkyl, cycloalkyl, R$^3$-aryl, R$^3$-arylalkyl, R$^3$-heteroaryl, R$^3$-heteroarylalkyl, heterocycloalkyl, heterocycloalkylalkyl, —C(O)OR$^{13}$, —C(O)NR$^{11}$R$^{12}$ and —C(O)R$^{16}$.

This invention also provides a pharmaceutical composition comprising an effective amount of at least one compound of formula I and a pharmaceutically acceptable carrier.

This invention further provides a method of treating: allergy, allergy-induced airway (e.g., upper airway) responses (e.g., pruritus, sneezing, rhinorrhea, mucosal inflammation; see, for example, McLeod, *JPET*, 305 (2003) 1037), congestion (e.g., nasal congestion), hypotension, cardiovascular disease, diseases of the GI tract, hyper- and hypomotility and acidic secretion of the gastro-intestinal tract, metabolic syndrome, obesity, sleeping disorders (e.g., hypersomnia, somnolence, and narcolepsy), disturbances of the central nervous system, attention deficit hyperactivity disorder (ADHD), hypo- and hyperactivity of the central nervous system (for example, agitation and depression), and/or other CNS disorders (such as Alzheimer's, schizophrenia, and migraine) comprising administering to a patient in need of such treatment an effective amount of at least one compound of formula I. "Patient" means a mammal, typically a human, although veterinary use is also contemplated.

Compounds of this invention are particularly useful for treating allergy, allergy-induced airway responses and/or congestion, obesity and metabolic syndrome.

This invention further provides a pharmaceutical composition comprising an effective amount of a combination of at least one compound of formula I and at least one H$_1$ receptor antagonist in combination with a pharmaceutically acceptable carrier.

This invention further provides a method of treating allergy, allergy-induced airway (e.g., upper airway) responses, and/or congestion (e.g., nasal congestion), comprising administering to a patient in need of such treatment (e.g., a mammal, such as a human being) an effective amount of a combination of at least one compound of formula I and at least one H$_1$ receptor antagonist.

Kits comprising a compound of formula I in a pharmaceutical composition and a separate H$_1$ receptor antagonist in a pharmaceutical composition in a single package are also contemplated.

In another aspect, the invention provides a pharmaceutical composition comprising effective amount of a combination of at least one compound of formula I and at least one other agent useful for treating obesity or metabolic syndrome in combination with a pharmaceutically acceptable carrier; a method of treatment of obesity or metabolic syndrome comprising administering to a patient in need of such treatment an effective amount of a combination of at least one compound of formula I and at least one other agent useful for treating obesity or metabolic syndrome is also contemplated, as are kits comprising in a single package a compound of formula I in a pharmaceutical composition and one or more agents for treating obesity or metabolic syndrome in one or more pharmaceutical compositions.

DETAILED DESCRIPTION OF THE INVENTION

Preferred definitions of the variables in the structure of formula I are as follows:
R is preferably R$^3$-phenyl, R$^3$-pyridyl, alkylthio, alkoxy, alkyl or haloalkyl. More preferably, R is pyridyl, especially 2-pyridyl. R$^3$ is preferably hydrogen, both on the "R" substituent and on the phenyl ring shown in formula I.
R$^1$ and R$^2$ preferably combine with the carbons to which they are attached to form an R$^6$-substituted phenyl ring. R$^6$ is preferably halo, more preferably fluoro. When $R^1$ and $R^2$ are not joined to form a ring, one of $R^1$ and $R^2$ is preferably $R^6$-phenyl and the other is H.

X is preferably —O—.

The variable "n" is preferably 3.

Z is preferably

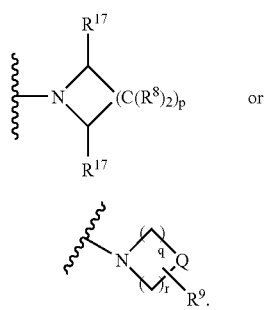

More preferably, Z is structure a), i.e., optionally substituted piperidinyl or optionally substituted pyrrolidinyl. When substituted, preferably 1 to 3 $R^8$ substituents are present selected from the group consisting of alkyl, hydroxyl, —NHC(O)alkyl, —C(O)NR$^{11}$R$^{12}$, —C(O)alkyl, —C(O)Oalkyl and heterocycloalkyl; each $R^{17}$ is preferably H. When $R^8$ is heterocycloalkyl, it is preferably piperidinyl or pyrrolidinyl.

As used herein, the following terms have the following meanings, unless indicated otherwise:

alkyl (including, for example, the alkyl portions of arylalkyl and alkoxy) represents straight and branched carbon chains and contains from one to six carbon atoms;

aryl (including the aryl portion of arylalkyl) represents a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is bound to the compound;

cycloalkyl represents saturated carbocyclic rings of from 3 to 6 carbon atoms;

halo represents fluoro, chloro, bromo and iodo;

haloalkyl means an alkyl as defined above wherein one or more hydrogen atoms on the alkyl are replaced by a halo group defined above. Chloroalkyl and fluoroalkyl refer to alkyl groups substituted by either chloro or fluoro groups, respectively, for example fluoroalkyl represents a straight or branched alkyl chain substituted by 1 to 5 fluoro atoms, which can be attached to the same or different carbon atoms, e.g., —CH$_2$F, —CHF$_2$, —CF$_3$, —CH$_2$CF$_3$ and —CF$_2$CF$_3$;

heteroaryl represents cyclic groups, having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms. The rings do not contain adjacent oxygen and/or sulfur atoms. Examples include but are not limited to isothiazolyl, isoxazolyl, oxazolyl, furazanyl, triazolyl, tetrazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoquinolinyl, quinolinyl, naphthyridinyl; all available substitutable carbon and nitrogen atoms can be substituted as defined;

heterocycloalkyl represents a saturated, carbocyclic ring containing from 3 to 15 carbon atoms, preferably from 4 to 6 carbon atoms, which carbocyclic ring is interrupted by 1 to 3 hetero atoms selected from —O—, —S—, —SO—, —SO$_2$— or —NR$^{40}$— wherein R$^{40}$ represents H, C$_1$ to C$_6$ alkyl, arylalkyl, —C(O)R$^{20}$, —C(O)OR$^{20}$, or —C(O)N(R$^{20}$)$_2$ (wherein each R$^{20}$ is independently selected); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

Ⓝ in the structure

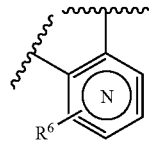

represents one or two nitrogen atoms located at one or two of the 4 non-fused positions of the ring, forming an azabenzimidazole or di-azabenzimidazole ring, respectively.

Similarly, Ⓝ a in the structure

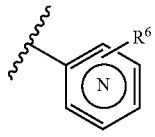

means that one or two nitrogen atoms are located at any one or two of the 5 available positions of the ring.

Also, as used herein, "upper airway" usually means the upper respiratory system—i.e., the nose, throat, and associated structures.

Also, as used herein, "effective amount" generally means a therapeutically effective amount.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($Cr_{6-24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

A line drawn into a ring means that the indicated bond may be attached to any of the substitutable ring carbon atoms.

The compounds of this invention are ligands for the histamine $H_3$ receptor.

The compounds of this invention can also be described as antagonists of the $H_3$ receptor, or as $H_3$ antagonists.

The compounds of this invention can be combined with an $H_1$ receptor antagonist (i.e., the compounds of this invention can be combined with an $H_1$ receptor antagonist in a pharmaceutical composition, or the compounds of this invention can be administered with an $H_1$ receptor antagonist).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxyloratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

Preferably, in the above methods, allergy-induced airway responses are treated.

In the methods of this invention wherein a combination of an $H_3$ antagonist of this invention (compound of formula I) is administered with an $H_1$ antagonist, the antagonists can be administered simultaneously or sequentially (first one and then the other over a period of time). In general, when the antagonists are administered sequentially, the $H_3$ antagonist of this invention (compound of formula I) is administered first.

The term "metabolic syndrome" refers to a combination of risk factors for cardiovascular disease (CVD) identified in the National Cholesterol Education Program's Adult Treatment Panel III report. See for example the discussion by Grundy et al in *Circulation,* 109 (2004), 433-438. The components of metabolic syndrome are: 1) abdominal obesity; 2) atherogenic dyslipidemia; 3) raised blood pressure; 4) insulin reistance; 5) proinflammatory state; and 6) prothrombotic state.

Other agents usful for treating obesity or metabolic syndrome include $CB_1$ antagonists, NPY5 antagonists, MCH antagonists, MC4R agonists and serotonin uptake inhibitors.

The compounds of Formula I can be prepared in many ways known to those skilled in the art. Following are typical procedures for preparing various compounds; other procedures may also be applicable and the procedures may be modified to prepare other compounds within the scope of Formula I. One skilled in the art will recognize that one route will be optimal depending on the choice of appendage substituents. Additionally, one skilled in the art will recognize that in some cases the order of steps has to be controlled to avoid functional group incompatibilities.

Unless otherwise stated, the following abbreviations have the stated meanings in the reactions schemes and examples below:

Me=methyl; Et=ethyl; Bu=butyl; Pr=propyl; Ph=phenyl; t-BOC=tert-butoxycarbonyl; and Ac=acetyl DEC=1-(3-dimethylaminopropyl)-3-ethylcarbodiimide hydrochloride DIPEA=diisopropylethylamine DMF=dimethylformamide DMSO=dimethylsulfoxide HOBT=1-hydroxybenzotriazole RT=room temperature TFA=trifluoroacetic acid THF=tetrahydrofuran TLC=thin layer chromatography HRMS=High Resolution Mass Spectrometry LRMS=Low Resolution Mass Spectrometry nM=nanomolar Ki=Dissociation Constant for substrate/receptor complex pA2=−logEC$_{50}$, as defined by J. Hey, *Eur. J. Pharmacol.*, (1995), Vol. 294, 329-335.

Ci/mmol=Curie/mmol (a measure of specific activity)

Compounds of the invention containing the benzimidazole or azabenzimidazole moiety wherein R is $R^3$-aryl, $R^3$-heteroaryl, $R^3$-cycloalkyl, $R^3$-heterocycloalkyl or alkyl can be prepared by the general procedure outlined in Scheme 1, wherein $R^3$, $R^6$, X, n and Z are as defined above (the scheme shows azabenzimidazole compounds, but it also applies to benzimidazole compounds).

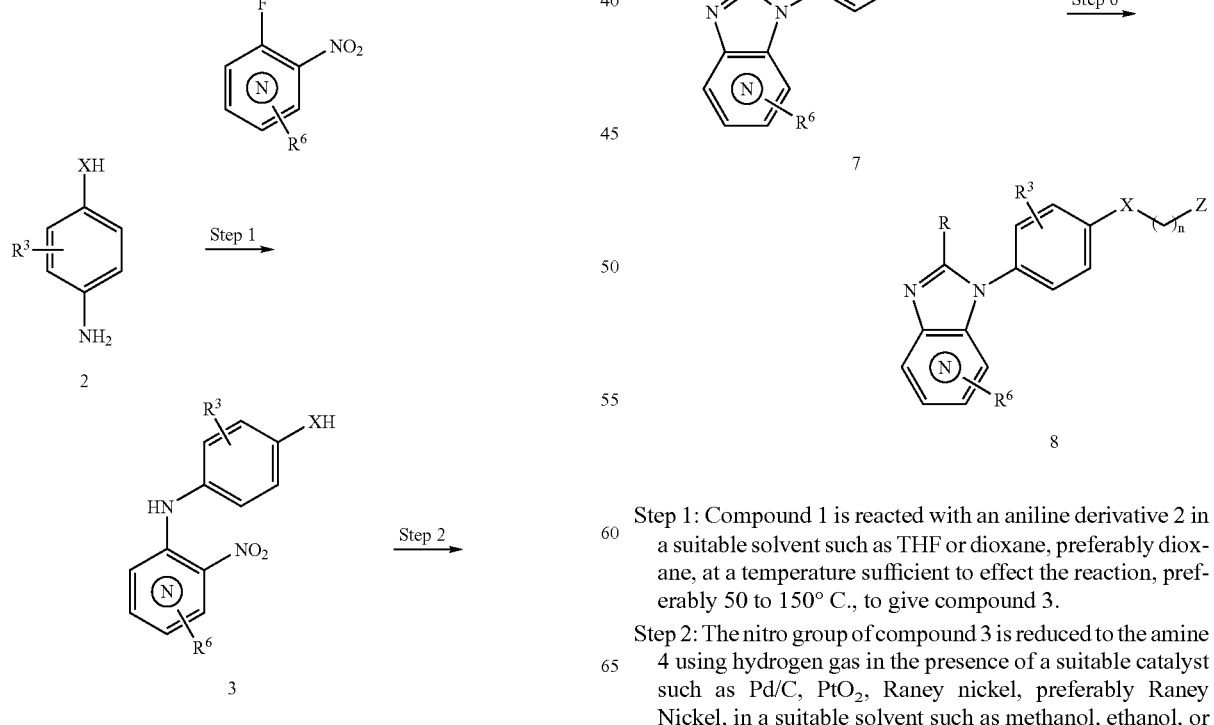

Step 1: Compound 1 is reacted with an aniline derivative 2 in a suitable solvent such as THF or dioxane, preferably dioxane, at a temperature sufficient to effect the reaction, preferably 50 to 150° C., to give compound 3.

Step 2: The nitro group of compound 3 is reduced to the amine 4 using hydrogen gas in the presence of a suitable catalyst such as Pd/C, PtO$_2$, Raney nickel, preferably Raney Nickel, in a suitable solvent such as methanol, ethanol, or isopropanol, preferably methanol or ethanol. Other reduction methods well known to those versed in the art are also suitable.

Step 3: The primary amine of compound 4 is acylated by reaction with a carboxylic acid in the presence of coupling agents such as DEC and HOBT in a suitable solvent such as ether, THF, or $CH_2Cl_2$, preferably $CH_2Cl_2$ to give compound 5. Alternatively, the amine can be acylated by an acid chloride in the presence of a base.

Step 4: In step 4, compound 5 in acetic acid is heated for a sufficient time for cyclization to occur.

Step 5: In step 5, if a protecting group is present on the group X, it is removed at this point. Suitable protecting groups for X=O, N, or S and methods for their removal can be found in Green's *Protecting Groups in Organic Synthesis*. Compound 6 is reacted with an α, ω-dihaloalkane in a suitable solvent such as acetone, THF, ether or the like, preferably acetone, in the presence of a base such as $Na_2CO_3$ or $K_2CO_3$, preferably $K_2CO_3$, at a temperature from 0 to 65° C. to give compound 7 wherein Y is halo.

Step 6: A solution of compound 7 in a suitable solvent such as $CH_3CN$, THF, ether, or the like, preferably $CH_3CN$, is treated with a tertiary amine base such as $Et_3N$, DIPEA or the like, preferably DIPEA, followed by the ZH, wherein Z is as defined above. The reaction is then heated at a temperature from 0 to 100° C. to give compound 8.

Substituted imidazole analogs can be prepared as shown in Scheme 2, wherein R, $R^3$ X, n and Z are as defined above, and wherein $R^1$ and $R^2$ are as defined above, but do not form a ring.

of a base such as $Na_2CO_3$ or $K_2CO_3$, preferably $K_2CO_3$, at a temperature from 0 to 65° C. to give compound 10.

Step 2: A solution of compound 10 in a suitable solvent such as $CH_3CN$, THF, ether, or the like, preferably $CH_3CN$, is treated with a tertiary amine base such as $Et_3N$, DIPEA or the like, preferably DIEPA, followed by the ZH, wherein Z is as defined above. The reaction is then heated at a temperature from 0 to 100° C. to give compound 11.

Compounds of the invention containing the benzimidazole or azabenzimidazole moiety wherein R is —$OR^4$ or —$SR^4$ can be prepared by the general procedure outlined in Scheme 3, wherein $R^3$, $R^6$, X, n and Z are as defined above (the scheme shows azabenzimidazole compounds, but it also applies to benzimidazole compounds).

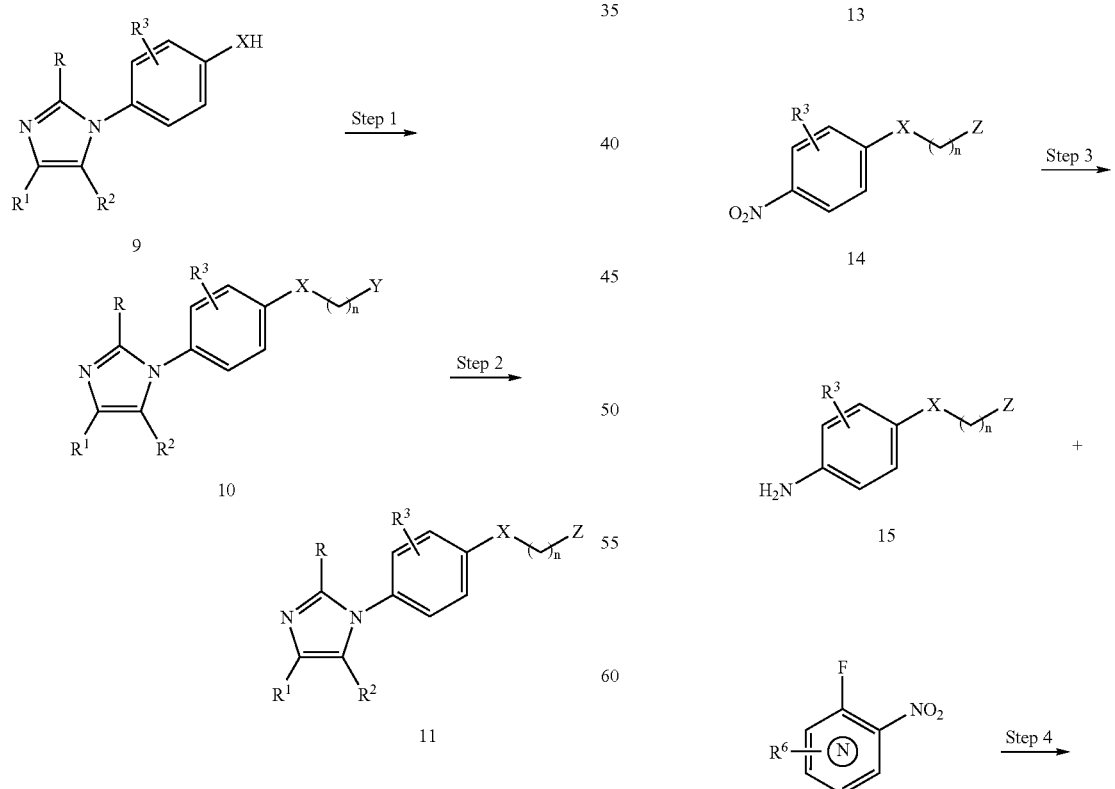

-continued

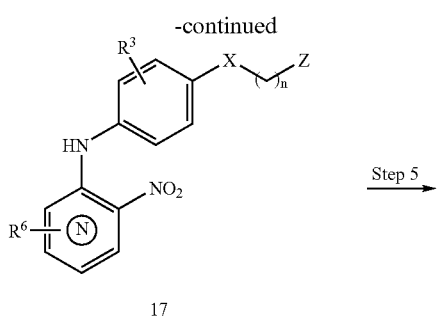

17

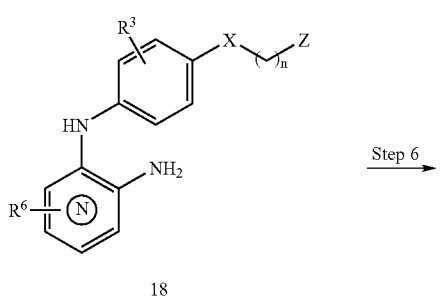

18

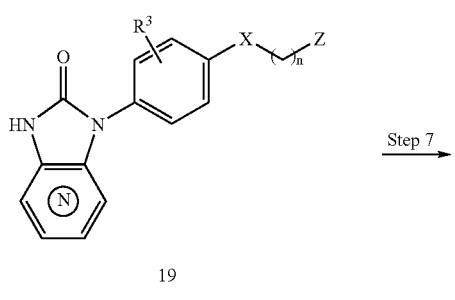

19

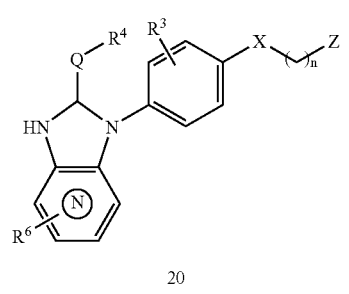

20

Step 1: In step 1, compound 12 is reacted with an α, ω-dihaloalkane in a suitable solvent such as acetone, THF, ether or the like, preferably acetone, in the presence of a base such as $Na_2CO_3$ or $K_2CO_3$, preferably $K_2CO_3$, at a temperature from 0 to 65° C. to give compound 13, wherein Y is halo.

Step 2: A solution of compound 13 in a suitable solvent such as $CH_3CN$, THF, ether, or the like, preferably $CH_3CN$, is treated with a tertiary amine base such as $Et_3N$, DIPEA or the like, preferably DIPEA, followed by the ZH, wherein Z is as defined above. The reaction is then heated at a temperature from 0 to 100° C. to give compound 14.

Step 3: The nitro group of compound 14 is reduced to the amine 15 using $H_2$ gas in the presence of a suitable catalyst such as Pd/C, $PtO_2$, or Raney nickel, preferably Raney Nickel, in a suitable solvent such as methanol, ethanol, or isopropanol, preferably methanol or ethanol. Other reduction methods well known to those versed in the art are also suitable.

Step 4: Compound 15 is reacted with 16 in a suitable solvent such as THF or dioxane, preferably dioxane, at a temperature sufficient to effect the reaction, preferably 50 to 150° C., to give compound 17.

Step 5: In a similar manner to Step 3, the nitro group of compound 17 is reduced to the amine to obtain compound 18.

Step 6: The amine 18 in a suitable solvent such as THF, ether or the like is treated with either thiocarbonyldiimidazole (Q=S) or 1,1'-carbonyldiimidazole (Q=O) at a temperature of from 0 to 100° C., preferably from 25 to 75° C., to give compound 19.

Step 7: A solution of 19 in a suitable solvent such as DMSO, DMF or the like is treated with a base such as $K_2CO_3$ or the like and an alkylating agent $R^4L$, in which L is Cl, Br or I, or a mesylate or sulfonate, at a temperature of 0 to 100° C., preferably from 25 to 75° C., to give 20.

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formula I can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

EXAMPLE 1

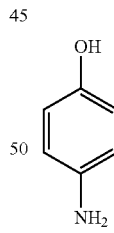 + 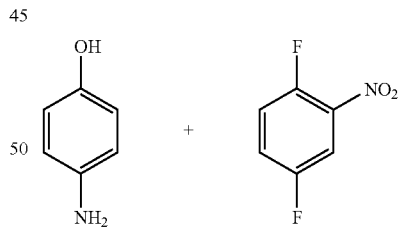 step 1→

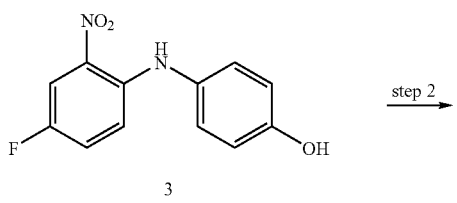 step 2→

-continued

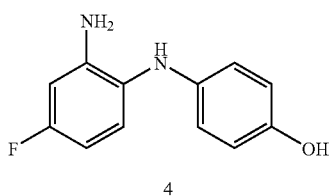

4

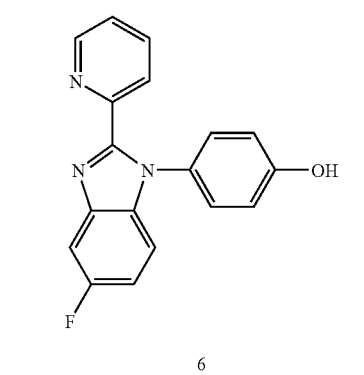

5

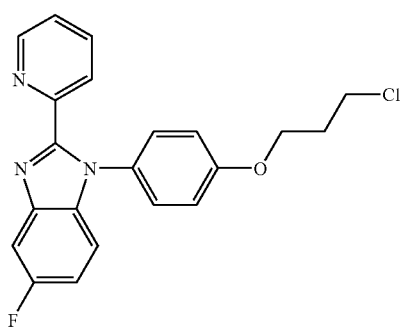

6

7

-continued

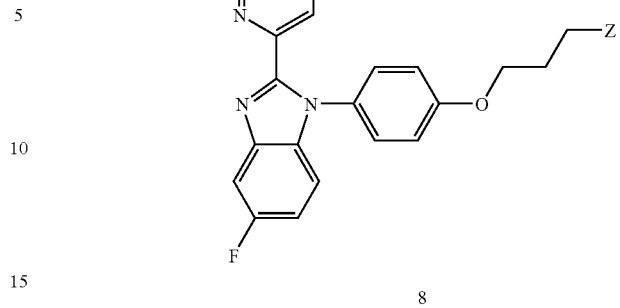

8

Step 1:
To a 1,4-dioxane (30 ml) solution of 1 (3.0 g, 27.50 mmol) at 25° C. was added 2 (4.4 g, 27.50 mmol). The mixture was refluxed under N₂ for 48 h. After cooling to RT, the products were concentrated in vacuo and purified by 40M Biotage Cartridge to give 3.

Step 2:
To a MeOH (50 ml) solution of 3 (4.4 g, 17.73 mmol) in a 500 ml hydrogenation bottle was added Ra—Ni (2.0 g) at 25° C. under N₂. The mixture was hydrogenated at 50 Psi H₂ for 20 h. The products were then filtered through celite, concentrated in vacuo, and purified by 40M Biotage Cartridge to give 4.

Step 3:
To a CH₂Cl₂ (50 ml) solution of 4 (3.2 g, 14.66 mmol) and picolinic acid (1.7 g, 14.66 mmol) were added DEC (3.9 g, 20.34 mmol) and HOBT (2.7 g, 20.34 mmol) at 25° C. After stirring under N₂ for 20 h, H₂O was added, the products were extracted with CH₂Cl₂ (2×), combined, then washed with brine, and dried over Na₂SO₄. The products were then filtered, concentrated in vacuo, and purified by 40M Biotage Cartridge to give 5.

Step 4:
A solution of compound 5 (2.1 g, 6.50 mmol) in 15 ml of acetic acid was heated at 120° C. under N₂ for 20 h. After cooling to RT, the product was concentrated in vacuo to give 6.

Step 5:
To an acetone (20 ml) solution of 6 (1.9 g, 6.22 mmol) was added K₂CO₃ (4.5 g, 32.48 mmol) at 25° C. After stirring under N₂ for 40 min, 1-bromo-3-chloropropane (1.3 ml, 12.99 mmol) was added, and the mixture was refluxed for 20 h. After cooling to RT, the products were then filtered, concentrated in vacuo, and purified by 40M Biotage Cartridge to give 7.

Step 6:
To 48-wells of a 96-well block of 1-ml glass tubes were added compound 7 (0.01 g, 0.026 mmol), MeCN (0.5 ml), and DIPEA (0.104 mmol). Then 1M stock solutions of each of the individual amines (shown in the table below) (0.053 ml, 0.053 mmol) were added to the tubes, which were then sealed and heated at 80° C. for 3 days. After cooling to RT, the solutions were transferred into 48-wells of a deep well polypropylene microtiter plate containing polystyrene isocyanate resin (2.5 equivalents, 0.066 mmol) and MP-carbonate resin (4 equivalents, 0.106 mmol). The microtiter plate was then sealed and shaken at 25° C. for 16 h. The solutions were then filtered through a polypropylene frit into a 96-well collection plate. The wells of the top plate were then washed with MeCN (0.5 ml), and the plate removed. After an aliquot of each solution was removed for LCMS analysis, the remaining solutions in the collection plate were transferred into vials and the solvents removed in vacuo via to provide amines 8.

Using the procedure describe above, the following compounds were prepared:

| Ex. | Starting Material | Product | Mass spec (M + H) |
|---|---|---|---|
| 1A | pyrrolidine | 6-fluoro-1-[4-(3-pyrrolidin-1-ylpropoxy)phenyl]-2-(pyridin-2-yl)-1H-benzimidazole | 417.23 |
| 1B | 3-hydroxypyrrolidine | 1-{3-[4-(6-fluoro-2-(pyridin-2-yl)-1H-benzimidazol-1-yl)phenoxy]propyl}pyrrolidin-3-ol | 433.24 |
| 1C | thiazolidine | 6-fluoro-1-[4-(3-thiazolidin-3-ylpropoxy)phenyl]-2-(pyridin-2-yl)-1H-benzimidazole | 435.24 |
| 1D | azepane | 1-[4-(3-azepan-1-ylpropoxy)phenyl]-6-fluoro-2-(pyridin-2-yl)-1H-benzimidazole | 445.24 |
| 1E | 1-cyclohexylpiperazine | 1-{4-[3-(4-cyclohexylpiperazin-1-yl)propoxy]phenyl}-6-fluoro-2-(pyridin-2-yl)-1H-benzimidazole | 514.28 |

-continued

| Ex. | Starting Material | Product | Mass spec (M + H) |
|---|---|---|---|
| 1F | 4-hydroxypiperidine | (structure) | 447.25 |
| 1G | thiomorpholine | (structure) | 449.25 |
| 1H | 3,5-dimethylpiperidine | (structure) | 459.25 |
| 1I | 3-acetamidopyrrolidine | (structure) | 474.26 |
| 1J | 1-methylhomopiperazine | (structure) | 460.25 |

-continued
| Ex. | Starting Material | Product | Mass spec (M + H) |
|---|---|---|---|
| 1K | 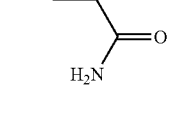 | 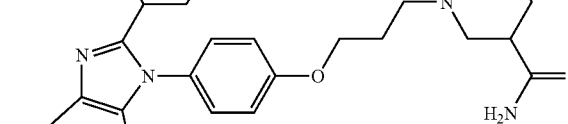 | 474.26 |
| 1L | 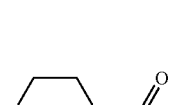 |  | 474.26 |
| 1M | 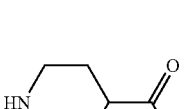 |  | 474.26 |
| 1N | 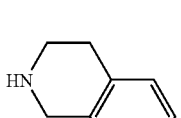 |  | 479.26 |
| 1O | 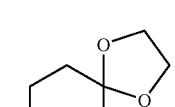 |  | 489.27 |

-continued

| Ex. | Starting Material | Product | Mass spec (M + H) |
|---|---|---|---|
| 1P | methyl piperidine-4-carboxylate | 5-fluoro-1-[4-(3-{4-(methoxycarbonyl)piperidin-1-yl}propoxy)phenyl]-2-(pyridin-2-yl)-1H-benzimidazole | 489.27 |
| 1Q | 4-(pyrrolidin-1-yl)piperidine | 5-fluoro-1-{4-[3-(4-pyrrolidin-1-ylpiperidin-1-yl)propoxy]phenyl}-2-(pyridin-2-yl)-1H-benzimidazole | 500.27 |
| 1R | 1-phenylpiperazine | 5-fluoro-1-{4-[3-(4-phenylpiperazin-1-yl)propoxy]phenyl}-2-(pyridin-2-yl)-1H-benzimidazole | 508.28 |
| 1S | 1-(pyridin-2-yl)piperazine | 5-fluoro-1-{4-[3-(4-pyridin-2-ylpiperazin-1-yl)propoxy]phenyl}-2-(pyridin-2-yl)-1H-benzimidazole | 509.28 |
| 1T | 2,6-dimethylmorpholine | 1-{4-[3-(2,6-dimethylmorpholin-4-yl)propoxy]phenyl}-5-fluoro-2-(pyridin-2-yl)-1H-benzimidazole | 461.25 |

-continued

| Ex. | Starting Material | Product | Mass spec (M + H) |
|---|---|---|---|
| 1U | | | 514.28 |
| 1V | | | 530.29 |
| 1W | | | 521.29 |
| 1X | | | 522.29 |
| 1Y | | | 526.29 |

-continued

| Ex. | Starting Material | Product | Mass spec (M + H) |
|---|---|---|---|
| 1Z | | | 537.3 |
| 1AA | | | 566.31 |
| 1BB | | | 518.28 |
| 1CC | | | 515.28 |

-continued
| Ex. | Starting Material | Product | Mass spec (M + H) |
|---|---|---|---|
| 1DD | 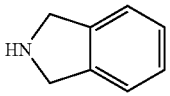 | 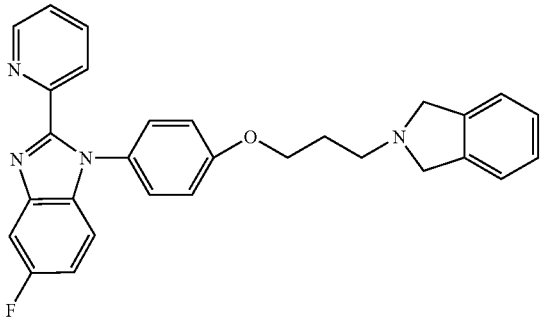 | 465 |
| 1EE |  | 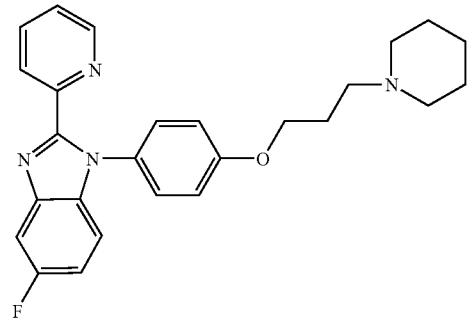 | 431 |
| 1FF | 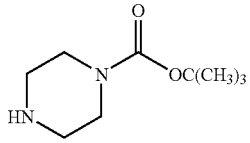 | 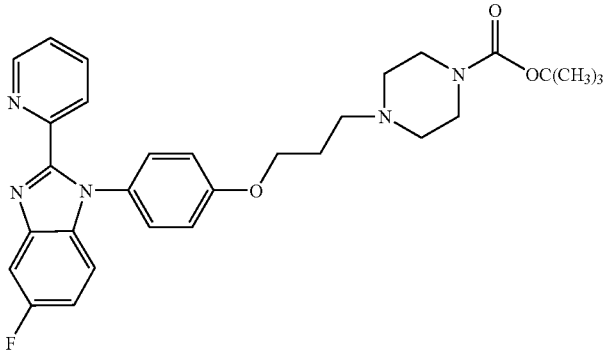 | 531 |
| 1GG |  | 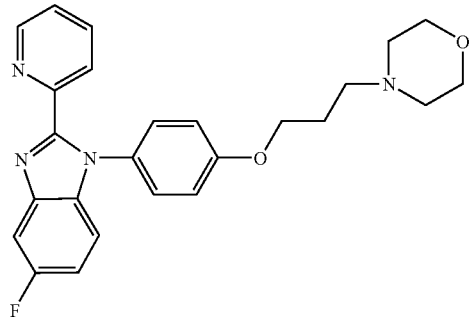 | 433 |

-continued

| Ex. | Starting Material | Product | Mass spec (M + H) |
|---|---|---|---|
| 1HH | | | 446 |
| 1II | | | 539 |
| 1JJ | | | 657 |
| 1KK | | | 586 |

-continued

| Ex. | Starting Material | Product | Mass spec (M + H) |
|---|---|---|---|
| 1LL | | | 565 |
| 1MM | | | 537 |
| 1NN | | | 566 |
| 1OO | | | 460 |

| Ex. | Starting Material | Product | Mass spec (M + H) |
|---|---|---|---|
| 1PP | | | 445 |

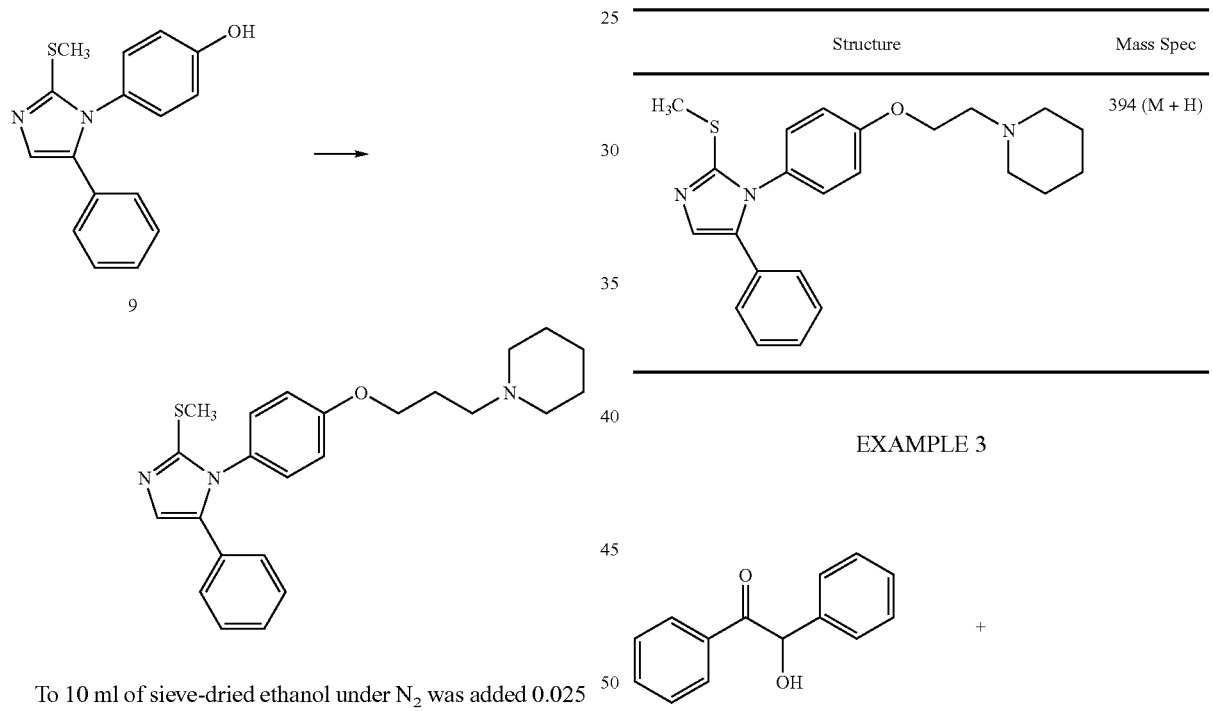

EXAMPLE 2

In a similar manner, Example 2A, was prepared:

| Structure | Mass Spec |
|---|---|
| 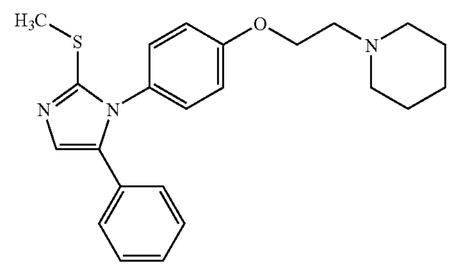 | 394 (M + H) |

To 10 ml of sieve-dried ethanol under $N_2$ was added 0.025 g (0.63 mmol) of 60% NaH (in oil dispersion) with stirring followed by addition of 9 (0.081 g, 0.29 mmol, DE 2803870). Stirring was maintained until a homogeneous solution was attained and then 1-(3-chloropropyl)piperidine hydrochloride (0.062 g, 0.31 mmol) was added. The mixture was heated under reflux for 18 h. TLC indicated the presence of starting material so additional phenol (21 mg) was added to the reaction mixture and the reaction was heated on a steam bath for 2 h. The reaction was concentrated in vacuo. The residue was treated with 0.5 N NaOH (50 ml) and extracted with ether. Combined extracts were washed with water, dried over anhydrous $MgSO_4$ (Darco), and concentrated to give 0.022 g viscous residue which was converted to the hydrochloride salt by the addition of 1N HCl in ether. The title compound was obtained (0.038 g). Mass spec: m/z 408 (MH+, 100%).

EXAMPLE 3

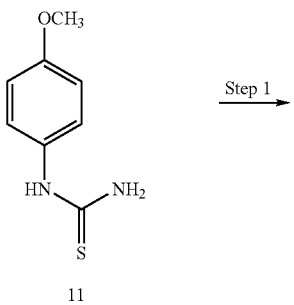

Step 1

-continued

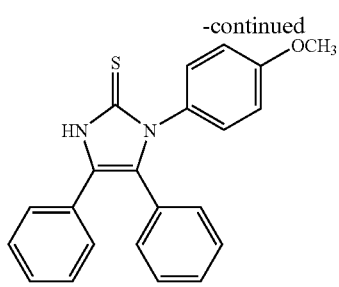

12

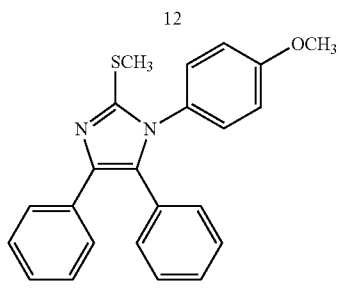

13

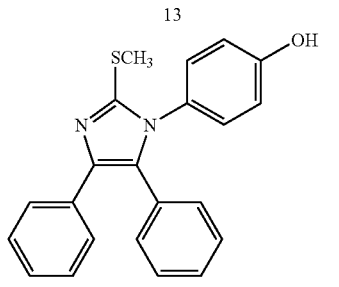

14

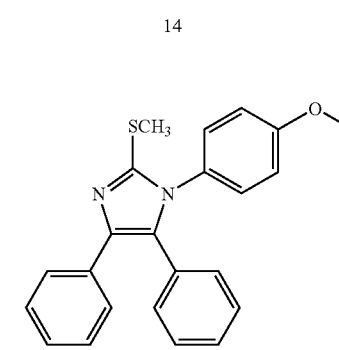

Step 1:
A mixture of 10 (11.66 g, 55 mmol) and 11 (10 g, 55 mmol) in DMF (30 ml) was heated to reflux for 1 h allowed to stand at RT for 48 h. A solid formed which was collected by filtration and washed with ethanol and hexane to give 12 (10.4 g, 52%) as a white solid. Mass spec: m/z 359 (MH+).

Step 2:
To a stirred suspension of 12 (10.1 g, 28.2 mmol) in methanol (400 ml) was added NaOH powder (2.5 g, 62 mmol). The reaction was warmed at 40° C. until a homogeneous solution was obtained. The reaction was cooled to RT and dimethyl sulfate (3.8 g, 30 mmol) was added dropwise. The mixture was stirred at RT for 1 h, diluted with water and the solid that formed was collected to obtain 13 (9.7 g, 92%). Mass spec: m/z 373 (MH+).

Step 3:
A solution of 13 (9.6 g, 25.8 mmol) in 30% HBr in AcOH (100 ml) was heated to reflux for 18 h. Most of the AcOH was removed using a Dean-Stark trap to give a solid. Water was added and the solid collected by filtration. The solid was dissolved in CH$_2$Cl$_2$ and washed with water. Concentration and purification via flash column chromatography (SiO$_2$, 5% MeOH in CH$_2$Cl$_2$) gave 14 (0.38 g). Mass spec: m/z 359 (MH+).

Step 4:
In a manner similar to that described in Step 2, 14 (0.17 g, 0.48 mmol) was converted to the title compound (0.13 g, 57%). Mass spec: m/z 484 (MH+).

EXAMPLE 4

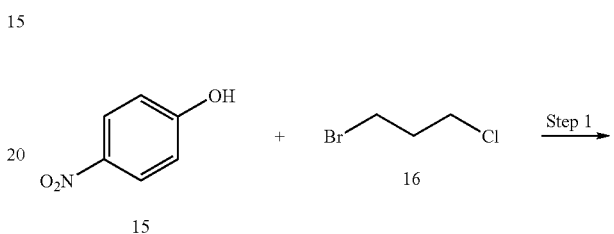

15    16

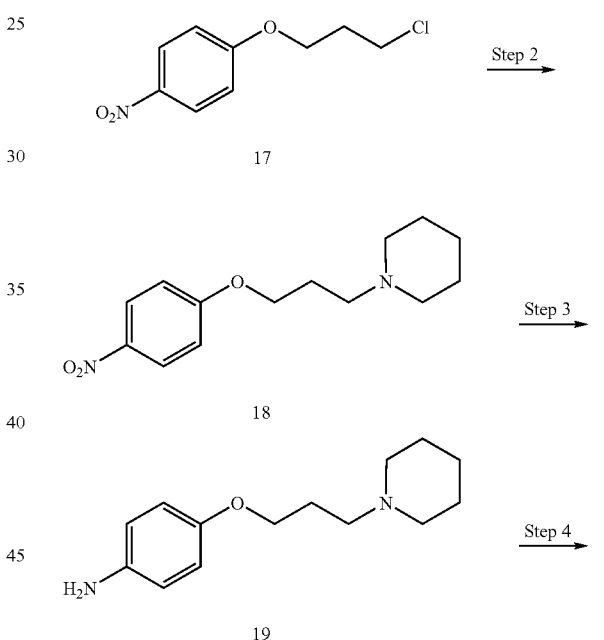

17

18

19

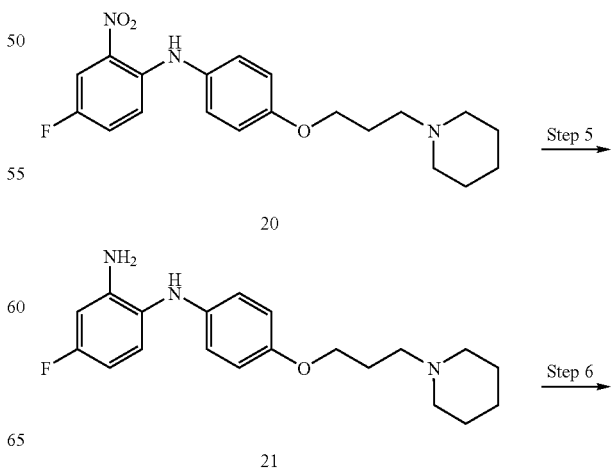

20

21

-continued

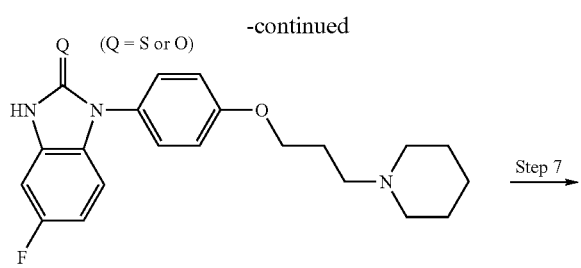

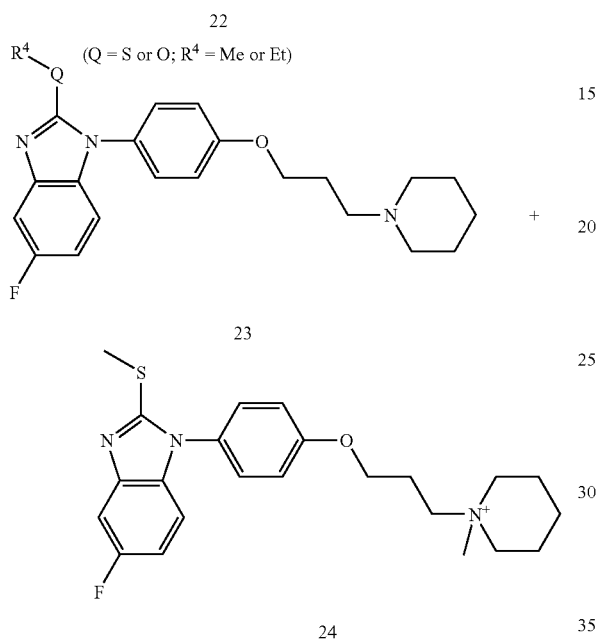

Step 1: K₂CO₃ (6.0 g, 43.2 mmol) was added to a solution of 15 (2.0 g, 14.4 mmol) and 16 (1.4 ml, 14.4 mmol) in acetone (50 ml) at 25° C. The mixture was refluxed under N₂ for 20 h. After cooling to RT, the products were filtered, the filtrate was concentrated in vacuum and purified by 40M Biotage Cartridge to give 17. Yield: 97%.

Step 2: To a solution of 17 (3.0 g, 13.9 mmol) and piperidine (2.8 ml, 27.8 mmol) in 30 ml of n-butanol at 25° C., Na₂CO₃ (1.4 g, 13.9 mmol) and NaI (0.04 g, 0.3 mmol) were added. The mixture was stirred at 100° C. under N₂ for 20 h. After cooling to RT, the products were filtered, the filtrate was concentrated in vacuum and purified by 40M Biotage Cartridge to give 18. Yield: 100%.

Step 3: Ra—Ni (1.0 g) was added to a MeOH (30 ml) solution of 18 (3.7 g, 14.0 mmol) at 25° C. in a 500 ml hydrogenation bottle. The mixture was hydrogenated at 50 Psi H₂ for 20 h. The products were then filtered through celite, and concentrated in vacuum to give 19. Yield: 85%.

Step 4: To a solution of 19 (2.8 g, 11.9 mmol) in 1,4-dioxane (30 ml) was added 2,5-difluoronitrobenzene (1.9 g, 11.9 mmol) at 25° C. The mixture was refluxed under N₂ for 72 h. After cooling to RT, the solvent was removed, the products were extracted with CH₂Cl₂ and H₂O, washed with brine, dried over Na₂SO₄, and filtered. The filtrate was concentrated in vacuum and purified by 40M Biotage Cartridge to give 20. Yield: 68%.

Step 5: The same procedure as step 3 was used to obtain 21. Yield: 94%.

Step 6: To a solution of 21 (0.5 g, 1.5 mmol) in THF (10 ml) was added 1,1'-thiocarbonyldiimidazole (0.7 g, 3.9 mmol) at 25° C. The mixture was stirred at 70° C. under N₂ for 20 h. After cooling to RT, the solvent was removed, the products were purified by 40S Biotage Cartridge to give 22 (Q=S). Yield: 98%.

Step 7: K₂CO₃ (0.2 g, 1.2 mmol) was added to a solution of 22 (0.3 g, 0.8 mmol) and CH₃I (0.9 mmol) in DMF (5 ml). The mixture was stirred at 25° C. under N₂ for 20 h. The product was extracted with EtOAc and H₂O, washed with brine, dried over Na₂SO₄, and filtered. The filtrate was concentrated in vacuum and purified by 40S Biotage Cartridge to give 23 (Q=S, R⁴=CH₃, Examples 4A and 4B).

EXAMPLE 4A

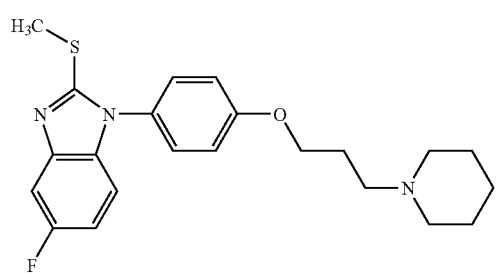

MH⁺: 400.1; yield: 7%.

EXAMPLE 4B

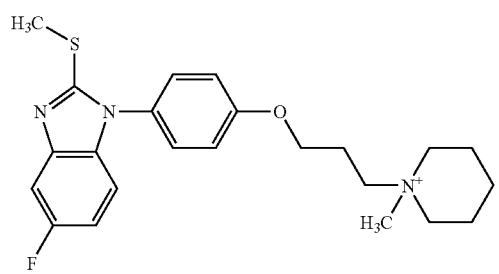

MH⁺: 414.1; yield 59%

Using a similar procedure and ethyl iodide in step 7, Example 4C was prepared:

EXAMPLE 4C

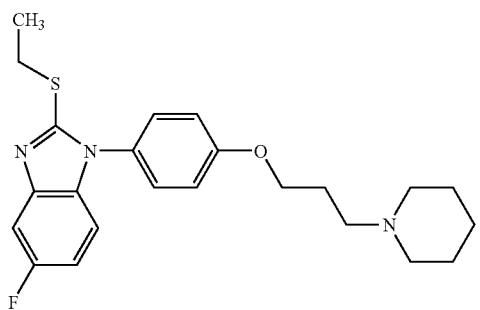

MH⁺: 414.1; yield 60%

Using a similar procedure but replacing 1,1'-thiocarbonyldiimidazole with 1,1'-carbonyldiimidazole in step 6 and using ethyl iodide in step 7, Example 4D was prepared:

EXAMPLE 4D

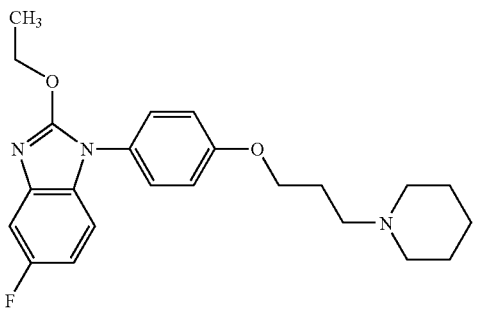

MH+: 398.1; yield 65%

General Procedure for $H_3$-Receptor Binding Assay

The source of the $H_3$ receptors in this experiment was guinea pig brain. The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-α-methyl histamine (8.8 Ci/mmol) or 3 nM [$^3$H]N$^α$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula I have a $K_i$ within the range of about 1 to about 1000 nM. Preferred compounds of formula I have a $K_i$ within the range of about 1 to about 100 nM. More preferred compounds of formula I have a $K_i$ within the range of about 1 to about 10 nM. The compound of Example 1EE has a $K_i$ of 1 nM.

In this specification, the term "at least one compound of formula I" means that one to three different compounds of formula I may be used in a pharmaceutical composition or method of treatment. Preferably one compound of formula I is used. Similarly, "at least one $H_1$ receptor antagonist" means that one to three different $H_1$, antagonists may be used in a pharmaceutical composition or method of treatment. Preferably, one $H_1$ antagonist is used.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of $H_3$ antagonist and $H_1$ antagonist compounds, the two active components may be co-administered simultaneously or sequentially, or a single pharmaceutical composition comprising a $H_3$ antagonist and an $H_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_1$ antagonist can be determined from published material, and may range from 1 to 1000 mg per dose. When used in combination, the dosage levels of the individual components are preferably lower than the recommended individual dosages because of the advantageous effect of the combination.

When separate $H_3$ and $H_1$ antagonist pharmaceutical compositions are to be administered, they can be provided in a kit comprising in a single package, one container comprising an $H_3$ antagonist in a pharmaceutically acceptable carrier, and a separate container comprising an $H_1$ antagonist in a pharmaceutically acceptable carrier, with the $H_3$ and $H_1$ antagonists being present in amounts such that the combination is therapeutically effective. A kit is advantageous for administering a combination when, for example, the components must be administered at different time intervals or when they are in different dosage forms.

Combinations with other agents for treating obesity or metabolic syndrome are prepared and administered in an analogous manner.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

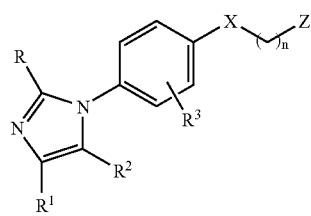

or a pharmaceutically acceptable salt thereof, wherein:

n is 2, 3, 4 or 5;

R is a 5- or 6-membered heteroaryl or heterocycloalkyl group, wherein one ring atom of the R group is nitrogen and the remaining ring atoms are carbon, and wherein the R group is optionally substituted with $R^3$;

$R^1$ and $R^2$ together with the carbon atoms to which they are attached form

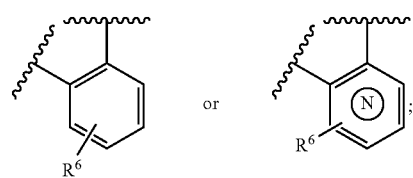

X is —O—, —S— or —$NR^7$—;

Z is

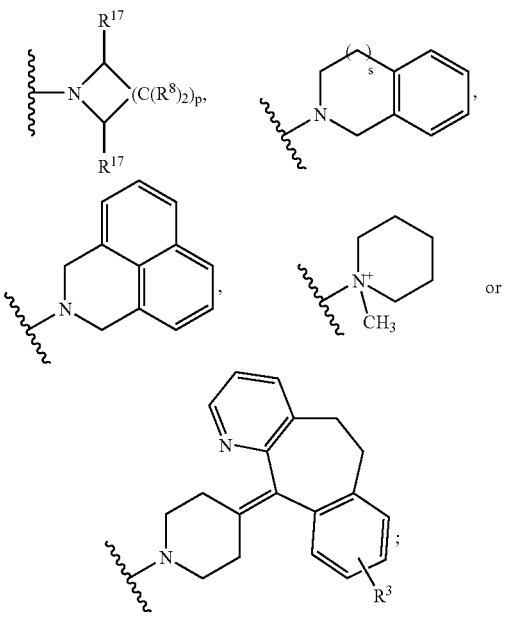

p is 1-3;
q is 1-4 and r is 1-4, provided that the sum of q and r is 3-6;
s is 1;
$R^3$ is 1-3 substituents independently selected from the group consisting of H, alkyl, halo, —OH, alkoxy and —$NR^{11}R^{12}$;
$R^6$ is 1-3 substituents independently selected from the group consisting of H, alkyl, —$CF_3$, halo, —$NO_2$, —CN, —C(O)$OR^{13}$, —C(O)$NR^{11}R^{12}$, —$NR^{14}R^{15}$, —$OR^{13}$ and haloalkyl;
$R^7$ is H, alkyl, —C(O)$OR^{13}$, —C(O)$NR^{11}R^{12}$ or —C(O)$R^{13}$;
each $R^8$ is independently selected from the group consisting of H, alkyl, cycloalkyl, $R^3$-aryl, $R^3$-arylalkyl, $R^3$-heteroaryl, heterocycloalkyl, -alkyl-heteroalkyl, -alkyl-heteroaryl, —$OR^{13}$, —C(O)$OR^{13}$, —$NR^{14}R^{15}$, —C(O)$NR^{11}R^{12}$, —C(O)$R^{16}$, C(=$NOR^{13}$)aryl and —C(=$NOR^{13}$)heteroaryl, wherein the heteroaryl moiety of an -alkyl-heteroaryl group is substituted with $R^3$; or two $R^8$ groups on the same carbon form a methylenedioxy or ethylenedioxy ring;
$R^{11}$ and $R^{12}$ are independently selected from the group consisting of H, alkyl, cycloalkyl, aryl and arylalkyl;
$R^{13}$ is H, alkyl, cycloalkyl or arylalkyl;
$R^{14}$ is H, alkyl, cycloalkyl or arylalkyl;
$R^{15}$ is H, alkyl, cycloalkyl, —C(O)$OR^{13}$, —C(O)$NR^{11}R^{12}$ or —C(O)$R^{13}$;
$R^{16}$ is H, alkyl, $R^3$-cycloalkyl, $R^3$-aryl, $R^3$-arylalkyl or $R^3$-heteroaryl;
each $R^{17}$ is independently selected from the group consisting of H, alkyl, cycloalkyl, $R^3$-aryl, $R^3$-arylalkyl, —C(O)$OR^{13}$, —C(O)$NR^{11}R^{12}$ and —C(O)$R^{16}$;
a heteroaryl group is defined as a 2- to 14-membered carbocyclic group having from 1 to 4 of it's ring carbon atoms independently replaced with an oxygen, nitrogen or sulfur atom such that the heteroaryl group does not have adjacent oxygen and/or sulfur ring atoms, and wherein all available carbon and nitrogen ring atoms can be substituted as defined above; and a heterocycloalkyl group is defined as a 3- to 15 -membered carbocyclic group having from 1 to 3 of it's ring carbon atoms independently replaced with —O—, —S—, —S(O)—, —S(O)$_2$— or N(R$^{40}$)—, wherein R$^{40}$ is H, C$_1$-C$_6$ alkyl or arylalkyl.

2. The compound of claim 1 wherein R is R$_3$-(2-pyridyl)-.

3. The compound of claim 2 wherein R is 2-pyridyl.

4. The compound of claim 1 wherein R$^1$ and R$^2$ combine with the carbons to which they are attached to form an R$^6$-substituted phenyl ring.

5. The compound of claim 4 wherein R$^6$ is halo.

6. The compound of claim 1 wherein X is —O—.

7. The compound of claim 1 wherein n is 3.

8. The compound of claim 1 wherein Z is R$^8$-piperidinyl or R$^8$-pyrrolidinyl.

9. The compound of claim 8 wherein Z is piperidinyl, pyrrolidinyl, R$^8$-piperidinyl or R$^8$-pyrrolidinyl wherein R$^8$ represents 1 to 3 substituents selected from the group consisting of alkyl, hydroxyl, —NHC(O)alkyl, —C(O)NR$^{11}$R$^{12}$, —C(O)alkyl, —C(O)Oalkyl and heterocycloalkyl.

10. A compound having the structure:

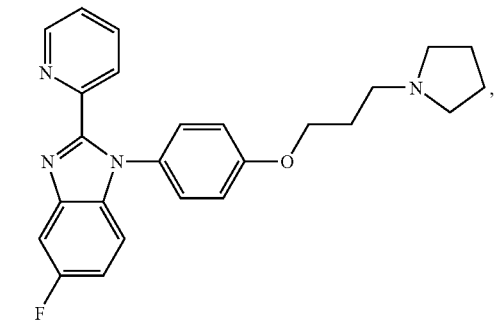

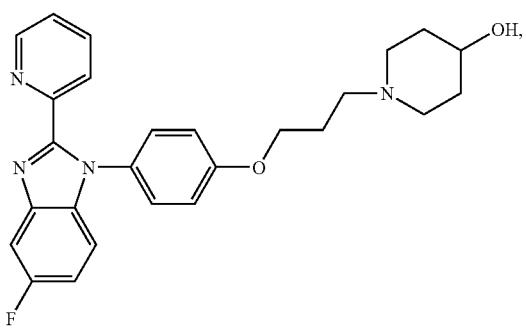

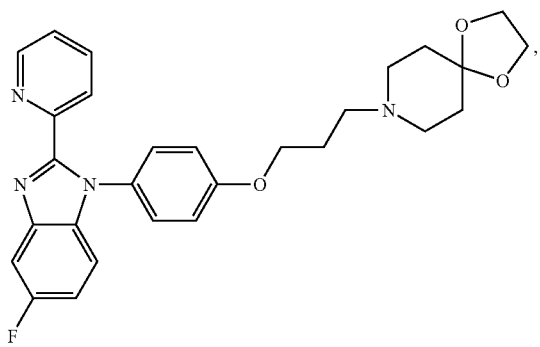

-continued

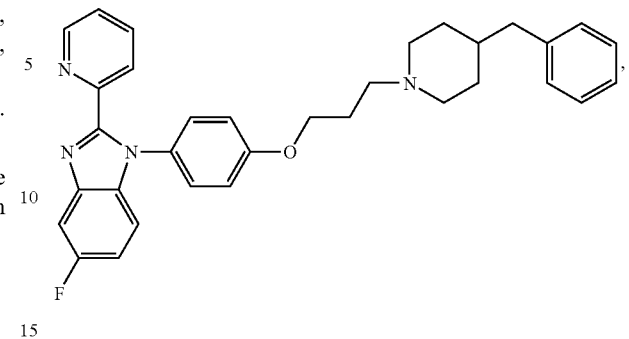

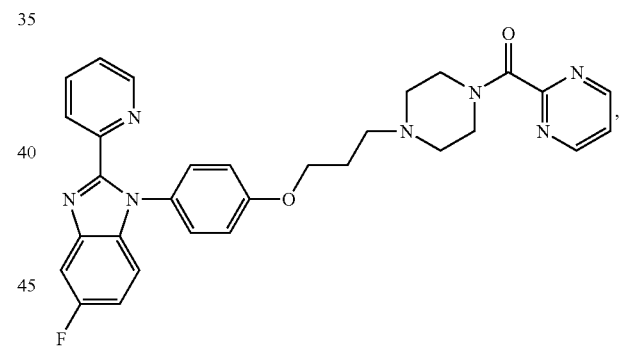

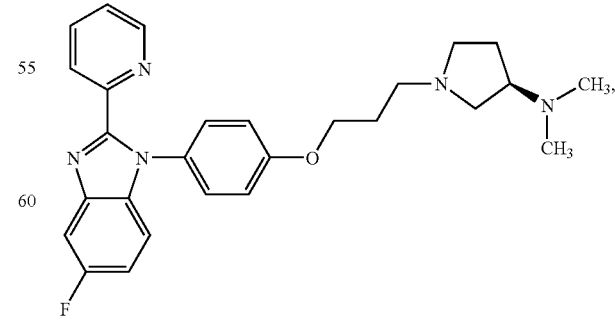

or

-continued

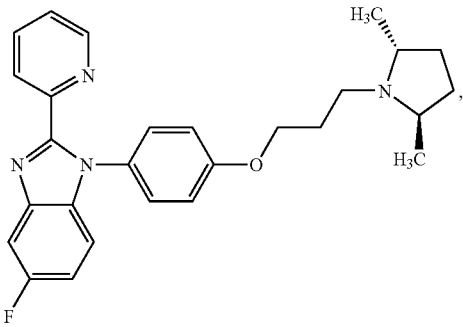

or a pharmaceutically acceptable salt thereof.

11. A pharmaceutical composition comprising an effective amount of a compound of claim 1 and a pharmaceutically effective carrier.

12. The pharmaceutical composition of claim 11, further comprising an effective amount of an $H_1$ receptor antagonist.

13. A pharmaceutical composition comprising an effective amount of a compound of claim 10 and a pharmaceutically effective carrier.

14. The pharmaceutical composition of claim 13, further comprising an effective amount of an $H_1$ receptor antagonist.

* * * * *